United States Patent
Vitek et al.

(10) Patent No.: US 6,613,004 B1
(45) Date of Patent: Sep. 2, 2003

(54) SYSTEMS AND METHODS FOR CREATING LONGER NECROSED VOLUMES USING A PHASED ARRAY FOCUSED ULTRASOUND SYSTEM

(75) Inventors: Shuki Vitek, Haifa (IL); Dov Maor, Haifa (IL)

(73) Assignee: InSightec-TxSonics, Ltd., Tirat Carmel (IL)

(*) Notice: Subject to any disclaimer, the term of this patent is extended or adjusted under 35 U.S.C. 154(b) by 0 days.

(21) Appl. No.: 09/557,078

(22) Filed: Apr. 21, 2000

(51) Int. Cl.⁷ .................................................. A61N 7/00
(52) U.S. Cl. ............................................. 601/2; 601/3
(58) Field of Search ..................... 601/2, 3, 4; 600/439, 600/459; 367/138

(56) References Cited

U.S. PATENT DOCUMENTS

| | | |
|---|---|---|
| 4,586,512 A | 5/1986 | Do-huu et al. |
| 4,858,597 A | 8/1989 | Kurtze et al. |
| 4,865,042 A * | 9/1989 | Umemura et al. |
| 4,888,746 A * | 12/1989 | Wurster et al. |
| 5,247,935 A | 9/1993 | Cline et al. |
| 5,275,165 A | 1/1994 | Ettinger et al. |
| 5,291,890 A | 3/1994 | Cline et al. |
| 5,305,737 A * | 4/1994 | Vago |
| 5,307,812 A | 5/1994 | Hardy et al. |
| 5,323,779 A | 6/1994 | Hardy et al. |
| 5,327,884 A | 7/1994 | Hardy et al. |
| 5,368,031 A | 11/1994 | Cline et al. |
| 5,368,032 A | 11/1994 | Cline et al. |
| 5,443,068 A | 8/1995 | Cline et al. |
| 5,490,840 A | 2/1996 | Uzgiris et al. |
| 5,507,790 A | 4/1996 | Weiss |
| 5,520,188 A | 5/1996 | Hennige et al. |
| 5,526,814 A | 6/1996 | Cline et al. |
| 5,553,618 A * | 9/1996 | Suzuki et al. .................. 601/3 |
| 5,590,657 A | 1/1997 | Cain et al. |
| 5,665,054 A | 9/1997 | Dory |
| 5,711,300 A | 1/1998 | Schneider et al. |

(List continued on next page.)

OTHER PUBLICATIONS

Charles A. Cain, et al., "Concentric–Ring and Sector–Vortex Phased–Array Applicators for Ultrasound Hyperthermia", IEEE Transactions on Microwave Theory and Techniques, MTT–34, pp. 542–551, 1986.

Todd Fjield, et al., "The Combined Concentric–Ring and Sector–Vortex Phased Array for MRI Guided Ultrasound Surgery", IEEE Transactions on Ultrasonics, Ferroelectircs and Frequency Control, vol. 44, No. 5, pp. 1157–1167.

Nathan McDannold, et al., "MRI Evaluation of Thermal Ablation of Tumors and Focused Ultrasound", JMRI vol. 8, No. 1, pp. 91–100, Jan./Feb. 1998.

Kullervo Hynynen et al., "Principles of MR–Guided Focused Ultrasound", Chapter 25, pp. 237–243.

(List continued on next page.)

*Primary Examiner*—Ruth S. Smith
(74) *Attorney, Agent, or Firm*—Bingham McCutchen LLP

(57) ABSTRACT

A system for performing a therapeutic procedure using focused ultrasound includes a transducer array including a plurality of transducer elements, drive circuitry coupled to the transducer elements, and a controller coupled to the drive circuitry. The controller controls the drive circuitry to alternatively provide sets of the transducer elements with respective drive signals. Each of the sets of transducer elements are alternatively driven with the respective drive signals for a predetermined duration during a sonication, while substantially continuously focusing ultrasonic energy produced by the transducer elements of each set at a desired focal zone. The controller also controls a phase component of the respective drive signals to provide a predetermined size, shape, and/or location of the focal zone, and thereby necrose a target tissue region at the focal zone.

24 Claims, 3 Drawing Sheets

U.S. PATENT DOCUMENTS

| | | | |
|---|---|---|---|
| 5,769,790 A | | 6/1998 | Watkins et al. |
| 5,873,845 A | | 2/1999 | Cline et al. |
| 5,885,211 A | * | 3/1999 | Eppstein et al. |
| 6,007,499 A | * | 12/1999 | Martin et al. |
| 6,142,939 A | * | 11/2000 | Eppstein et al. |

OTHER PUBLICATIONS

Harvey E. Cline, Ph.D., et al., "Focused US System for MR Imaging–Guide Tumor Ablation", Radiology vol. 194, No. 3, pp. 731–738, Mar. 1995.

* cited by examiner

SYSTEMS AND METHODS FOR CREATING LONGER NECROSED VOLUMES USING A PHASED ARRAY FOCUSED ULTRASOUND SYSTEM

FIELD OF THE INVENTION

The present invention relates generally to systems and methods for performing noninvasive surgical procedures using focused ultrasound, and more particularly to systems and methods for creating longer necrosed volumes using a focused ultrasound transducer array.

BACKGROUND

High intensity focused acoustic waves, such as ultrasonic waves (acoustic waves with a frequency greater than about 20 kilohertz), may be used to therapeutically treat internal tissue regions within a patient. For example, ultrasonic waves may be used to ablate tumors and obviate the need for invasive surgery. In order to generate sufficient energy to ablate or necrose tissue, piezoelectric transducers have been used. Such transducers are placed external to the patient but in close proximity to the tissue to be ablated and are driven by electric signals to produce ultrasonic energy. The transducer is geometrically shaped and positioned such that the ultrasonic energy is focused at a focal zone corresponding to a target tissue region within the patient, heating the target tissue region until the tissue is necrosed. The transducer may be sequentially focused and activated at a number of focal zones in close proximity to one another. This series of sonications is used to cause coagulation necrosis of an entire tissue structure, such as a tumor, of a desired size and shape.

A spherical cap transducer array, such as that disclosed in U.S. Pat. No. 4,865,042 issued to Umemura et al., has been suggested for this purpose. This spherical cap transducer array includes a plurality of concentric rings disposed on a curved surface having a radius of curvature defining a portion of a sphere. The concentric rings generally have equal surface areas and may also be divided circumferentially into a plurality of curved transducer elements or sectors, creating a sector-vortex array. The transducer elements are all simultaneously driven by radio frequency (RF) electrical signals at a single frequency offset in phase and amplitude. In particular, the phase and amplitude of the respective drive signals may be controlled so as to focus the emitted ultrasonic energy at a desired focal zone and provide a desired energy level in the target tissue region.

To increase the size of the necrosed region, the amplitude of the respective drive signals may be increased, thereby directing more ultrasonic energy at the focal zone. This generally increases the size of the tissue region that is necrosed at the focal zone by the sonication, and consequently may reduce the number of sonications needed to treat an entire tissue structure, such as a tumor. Increasing the amplitude, however, also increases the amount of energy that passes through the tissue on either side of the focal zone. This may cause undesired pain to the patient, heating, and/or necrosis of tissue outside of the target region, particularly in the "near field," i.e., the region between the transducer and the focal zone.

As an alternative, to increase the necrosed volume per sonication, a spherical cap transducer array has been suggested that is divided circumferentially into a plurality of "sectors," such as that disclosed in U.S. Pat. No. 4,865,042 issued to Umemura et al. The phase of the respective drive signals to each of the sectors may be controlled to create a desired size and shape for the focal zone. For example, if each of the sectors are driven with respective drive signals that are in phase with one another ("mode 0"), the ultrasonic energy may be focused substantially at a relatively narrow focal zone, similar to the concentric ring transducer array described above.

Alternatively, the sectors may be driven with respective drive signals that are in a predetermined phase relationship with one another (referred to as "out of phase" or "mode n"). This results in a focal zone that generally has a ring shape, creating a wider focus that causes necrosis of a larger tissue region within a focal plane intersecting the focal zone. Achieving adequate necrosis within this larger focal zone, however, requires increasing the total sonication energy (increasing sonication power and/or duration), which may also increase the heating of tissue outside the target tissue region, because more energy may flow through the funnels on either side of the focal zone. This may require additional cooling time between sonications to prevent build-up of heat, particularly within the tissue in the near field.

To increase the size of the necrosed volume in a direction substantially perpendicular to the focal plane, a method known as "apodization" has been suggested. Apodization involves activating only an inner set of rings within a concentric ring array during a sonication, i.e., shutting down one or more of the outer rings for the entire duration of the sonication. This effectively raises the "f-number" of the transducer array (f-number is the ratio of the radius of curvature to the size of the "aperture" or diameter of the transducer array), producing a narrower funnel through which the ultrasonic energy passes between the transducer and the focal zone. When the same total amount of energy is focused at the focal zone using apodization, a longer necrosed volume results. However, the narrower funnel may also increase the risk of excessive heating of the tissue on either side of the focal zone, particularly in the near field.

Accordingly, it would be desirable to provide systems and methods for treating a tissue region using ultrasound energy that may increase the necrosed volume, without substantially increasing the risk of heating outside the focal zone.

SUMMARY OF THE INVENTION

The present invention is directed to systems and methods for performing a therapeutic procedure using focused ultrasound that increases the necrosed volume, without substantially increasing heating of tissue outside of the focal zone.

In a preferred embodiment, a focused ultrasound system includes a transducer array including a plurality of transducer elements. Drive circuitry is coupled to the transducer elements, the drive circuitry configured for providing respective drive signals to each of the transducer elements. A controller is provided for alternatively directing ultrasonic energy from sets of the transducer elements towards a patient being treated. Preferably, the controller is coupled to the drive circuitry, the controller configured for controlling the drive circuitry to alternatively provide each set of transducer elements with respective drive signals.

The controller may also be configured for controlling a phase component of respective drive signals provided to the transducer elements to provide a predetermined size and shape of a focal zone created by the transducer elements and/or to focus the transducer elements in each of the sets substantially at a desired focal location. The controller may include a selector for alternatively coupling one of the sets of transducer elements to the drive circuitry, whereby the drive circuitry may provide respective drive signals to the coupled set of transducer elements, and/or the controller may include a microprocessor for electronically controlling the drive circuitry.

In an exemplary embodiment, the transducer array may be a concentric ring array including a plurality of sets of concentric annular transducer elements or rings. Each of the concentric rings may be divided circumferentially into a plurality of curved elements or "sectors." Alternatively, other shapes, arrangements, or geometries of transducer elements may be provided that may be divided into sets.

Each of the sets of transducer elements may be alternatively driven with a set of respective drive signals for a predetermined duration during a sonication, while substantially continuously focusing ultrasonic energy produced by the transducer elements of each set at a desired focal zone. Consequently, the resulting necrosed tissue region at the focal zone may be substantially increased in volume, while distributing the energy along separate funnels that substantially reduce the risk of undesired heating and/or necrosis outside the focal zone.

Other objects and features of the present invention will become apparent from consideration of the following description taken in conjunction with the accompanying drawings.

BRIEF DESCRIPTION OF THE DRAWINGS

Preferred embodiments of the present invention are illustrated by way of example, and not by way of limitation, in the figures of the accompanying drawings, in which like reference numerals refer to like components, and in which.

DETAILED DESCRIPTION OF THE PREFERRED EMBODIMENTS

Figure 1:
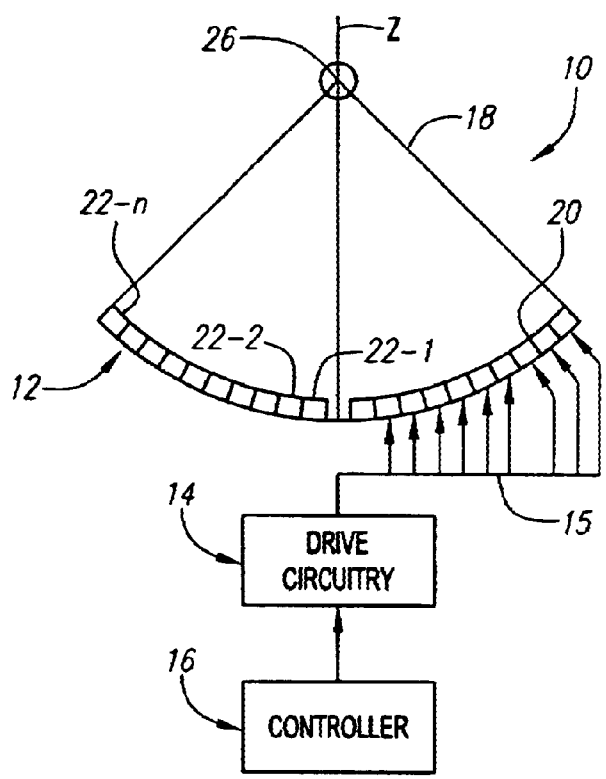
FIG. 1 is a schematic diagram of a focused ultrasound system, in accordance with the present invention.
Figure 2A:
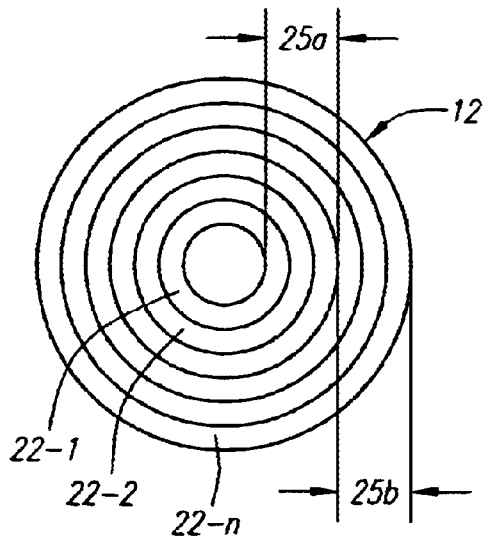
FIG. 2A is a top view of a first preferred embodiment of a transducer array for the focused ultrasound system of FIG. 1.

Turning now to the drawings, FIGS. 1 and 2A show an exemplary embodiment of a system 10 for performing a therapeutic procedure using focused ultrasound, in accordance with the present invention. The system 10 generally includes a transducer 12, drive circuitry 14 for providing electrical drive signals 15 to the transducer 12, and a controller 16 for controlling the drive signals 15 provided by the drive circuitry 14. The transducer 12 is preferably a phased array ultrasound transducer formed from piezoelectric material, constructed as is known to those skilled in the art. The transducer 12 includes a plurality of "n" individual transducer elements 22 (n being an integer greater than one defining the total number of transducer elements 22), the transducer elements 22 being coupled to the drive circuitry 14 in a conventional manner.

In the exemplary embodiment shown in FIGS. 1 and 2A, the transducer 12 has a substantially concave or bowl shape, preferably a "spherical cap" shape, i.e., having a substantially constant radius of curvature 18 such that the transducer 12 has an inside surface 20 defining a portion of a sphere. Alternatively, the transducer may be substantially flat, elongate, or may have other desired overall shapes (not shown).

As shown in FIG. 2A, the transducer elements 22 may be provided in the shape of concentric rings 22-1 to 22-n, for example, by cutting concentric circles through a piezoelectric shell (not shown). Preferably, the rings 22-1 to 22-n have substantially the same surface area as one another, and thus, the widths of the rings 22-1 to 22-n are progressively smaller from the innermost ring 22-1 outward to the outermost ring 22-n. Alternatively, rings 22-1 to 22-n having widths that are substantially equal to one another, or other ring configurations (not shown) may be provided. Any spaces (not shown) between the rings 22-1 to 22-n may be filled with silicone rubber and the like to substantially isolate the rings 22-1 to 22-n from one another.

In a preferred embodiment, the transducer 12 has an outer diameter of between about 8–12 cm, a radius of curvature 18 between about 8–16 cm, and includes between about ten and thirty rings 22-1 to 22-n. Additional information on the construction of a concentric ring phased array transducer appropriate for use with the present invention may be found, for example, in C. Cain and S. Umemura, "Concentric-Ring and Sector-Vortex Phased-Array Applicators for Ultrasound Hyperthermia," IEEE Transactions on Microwave Theory and Techniques, vol. MTT-34, no. 5, pages 542–551 (May 1986), the disclosure of which is expressly incorporated herein by reference.

Figure 2B:
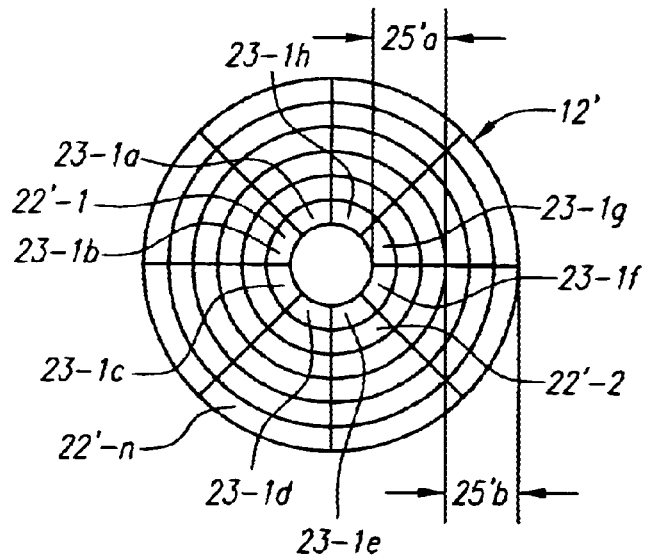
FIG. 2B is a top view of a second preferred embodiment of a transducer array for the focused ultrasound system of FIG. 1.

In alternative embodiments, the transducer elements 22 may have other shapes, arrangements, or geometries. For example, turning to FIG. 2B, an alternative embodiment of a concentric ring transducer array 12' is shown that is divided circumferentially into curved elements or "sectors" 23. Each ring 22'-1 to 22'-n of the transducer 12' may be divided circumferentially into sectors 23 (23-1a to 23-1h being illustratively shown for the innermost ring 22-1 in FIG. 2B). For example, radial cuts may be made in the transducer, as described above, or thin radial strips of electrode (not shown) may be removed from the back of the transducer 12' between each sector 23. Such transducers are shown, for example, in T. Fjield and K. Hynynen, "The Combined Concentric-Ring and Sector-Vortex Phased Array for MRI Guided Ultrasound Surgery," IEEE Transactions on Ultrasonics, Ferroelectrics, and Frequency Control, vol. 44, no. 5, pages 1157–1167 (Sept. 1997), the disclosure of which is expressly incorporated herein by reference.

In a further alternative embodiment, a spherical cap or other transducer may be divided into a plurality of transducer elements having other shapes or arrangements (not shown), such as a checkerboard pattern, a hexagonal lattice, or even a substantially random pattern of transducer elements. In still further alternatives, a linear array of transducer elements (not shown) may be provided. The transducer elements may have substantially the same size or surface area, or different size transducer elements may be provided. Thus, the individual transducer elements may have any desired individual geometry or shape, and/or any desired overall lay-out with respect to one another.

Returning to FIG. 1, the controller 16 is coupled to the drive circuitry 14 for controlling several aspects of the drive signals 15 generated by the drive circuitry 14. First, the controller 16 may control the amplitude of the drive signals 15, for example, to control the intensity of ultrasonic energy delivered by the transducer 12. In addition, the controller 16 may control the phase between each of the transducer elements 22. For example, by shifting the phase between the concentric rings 22-1 to 22-n, shown in FIG. 2A, a location or "focal distance" of a focal zone 26 (i.e., the distance from the transducer 12 to the focal zone 26) created by the ultrasonic energy produced by the transducer 12 may be adjusted along the z axis, as is shown in FIG. 1. In addition, for the embodiment shown in FIG. 2B, the controller 16 may shift the phase between the sectors 23, or change the "mode" of the transducer 12', to control the size and shape of the focal zone created by the ultrasonic energy, as is known to those skilled in the art. The controller 16 may include a processor, such as a microcomputer (not shown), that is coupled to the drive circuitry 14 for controlling these aspects of its operation. Further information on phase shifting of phased array transducers may be found in the Cain article referenced above, as well as in U.S. Pat. No. 4,865,042 issued to Umemura et al., the disclosure of which is also expressly incorporated herein by reference.

The controller 16 also preferably effectively divides the transducer 12 into a plurality of sets of transducer elements 22. For example, the controller 16 may direct the drive circuitry 14 to alternatively or sequentially activate each of the sets, i.e., to alternatively drive only those specific transducer elements 22 included in each respective set, during the course of a single sonication. Alternatively, as described further below, the controller may control a mechanical shutter device (not shown) to alternatively or sequentially expose a patient being treated to the ultrasonic energy generated by specific transducer elements 22 included in respective sets. Thus, the controller effectively activates less than all of the transducer elements 22 at any one time, but alternatively, sequentially, and/or selectively activates individual sets during a single sonication, as explained further below.

Each set includes a plurality of "m" transducer elements ("m" being an integer greater than one, and less than "n," the total number of transducer elements). The sets may be predefined, e.g., fixed such that the same group of transducer elements are always associated with the same respective set. Alternatively, the controller 16 may define the sets in any desired manner, for example, by dividing the transducer elements randomly into sets that may defined at the beginning of a sonication or during the course of a sonication.

For example, the controller 16 may divide the transducer 22 into sets that each have the same number of transducer elements 22 or into sets that each have the same overall surface area. Preferably, the transducer elements 22 are all of the same individual surface area, and therefore each set may include the same number of transducer elements and the same overall surface area. This may ensure that the ultrasonic energy delivered during a sonication remains substantially constant. In one embodiment, the controller 16 may divide the transducer 12 into "p" sets ("p" being an integer greater than one), each set including "n/p" transducer elements, and/or the controller 16 may divide the transducer 12 into "p" sets, each set having an overall surface area "a" that is "A/p" ("A" being the overall surface area of the entire transducer 12).

Because each of the sets has a surface area "a" that is less than "A", the "f-number" "$f_m$" of each of the sets is effectively higher as compared to the f-number "$f_n$" of the entire transducer 12. F-number of a transducer is defined as the ratio of the focal distance to the "aperture" ("aperture" being the diameter or other effective cross-sectional dimension proportional to a square root of the surface area) of the transducer. Thus, as the surface area, and consequently the size of the aperture, of the transducer is reduced, e.g., when fewer than all of the transducer elements are simultaneously activated, the f-number is effectively substantially increased for a given focal distance.

For examples, with respect to the exemplary system 10 of FIG. 2A, the controller 16 may divide the transducer 12 into two sets, an inner set 25a of concentric rings 22-1 to 22-(n/2), and an outer set 25b of concentric rings 22-(n/2+1) to 22-n. Each set 25a, 25b may have the same number of rings ("n/2") and/or may have substantially the same overall surface area ("a=A/2"). Alternatively, three or more sets of concentric rings ("p" =3, 4, 5, etc.) may be provided (not shown), with each set including a plurality of rings. The rings in each respective set may be disposed adjacent one another, although alternatively, any "n/p" rings may be selected for each respective set.

The controller 16 controls the drive circuitry 14 to alternatively provide drive signals 15 to the inner and outer sets 25a, 25b, while focusing the ultrasonic energy produced by the respective transducer elements 22 at a focal zone 26 (see FIG. 1). The controller 16 may include a processor to control the drive circuitry 14, and/or may include a selector or other switching device that alternatively couples one of the sets 25a, 25b to the drive circuitry 14.

During a single sonication, which may last as long as about five seconds or more, and preferably about ten seconds or more, the controller 16 may alternatively and/or sequentially activate the inner and outer sets 25a, 25b of rings 22, preferably for not more than about one second, and more preferably, for about 0.2–0.5 seconds. At the same time, the controller 16 may control the phase (for a periodic continuous wave signal, or more broadly, delay), and/or amplitude of the drive signals 15 to maintain the focal zone of the resulting ultrasonic energy generated by the transducer 12 at a target tissue region within a patient's body. Thus, the controller 16 may direct the drive circuitry 14 to provide a plurality of alternate sets of drive signals 15, each activating a different set of rings.

Because each set 25 of rings 22 is activated separately, each set 25 of rings 22 behaves as if it had a substantially higher f-number, as explained above. Thus, the ultrasonic energy delivered from each set 25 of rings 22 travels through relatively narrow funnels, producing a relatively long focal zone compared to operating all of the rings 22 simultaneously. In addition, because of the different geometry of the inner and outer sets 25a, 25b of rings 22, the respective narrow funnels pass through different tissue regions (as may be seen in FIG. 3D). This more widely distributes the heat generated in the tissue on either side of the focal zone in the respective funnels, which may substantially minimize undesired heating and/or reduce the cooling time required between sonications.

Alternatively, the controller 16 may define each set of transducer elements as it proceeds through a single sonication and may activate the defined sets in a desired sequence or pattern. For example, the controller 16 may randomly assign any number less than all of the transducer elements 22 defining the entire transducer to a particular set and then activate that set while it defines the next set. Thus, a single sonication may be divided into a plurality of sequential pulses that are created by the respective sets as they are defined and activated.

The focal zone A created by a system 10 in accordance with the present invention is illustrated in FIGS. 3A–3E, which compare the funnel shapes of a similarly dimensioned concentric ring transducer array operated in various modes.

Figure 3A:
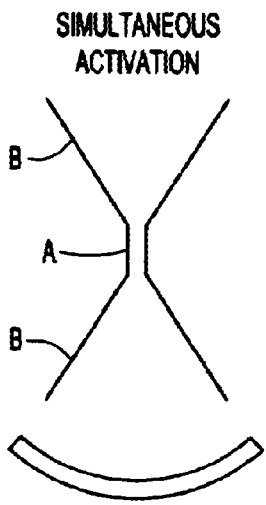
FIGS. 3A–3E are schematic illustrations showing relative funnel shapes of the ultrasonic energy delivered by alternative embodiments of spherical cap transducer arrays.
Figure 3B:
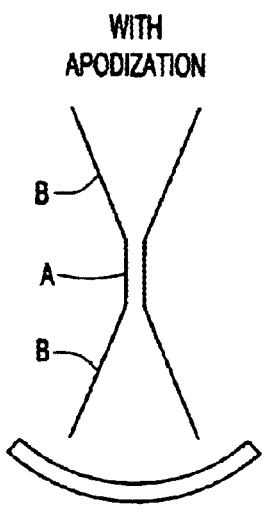
Figure 3C:
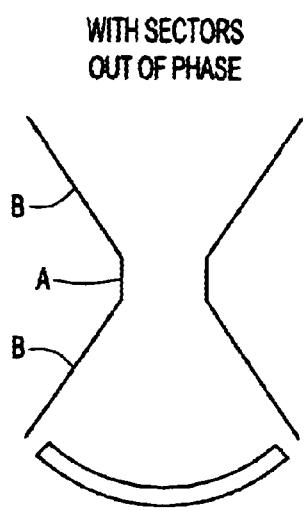
Figure 3D:
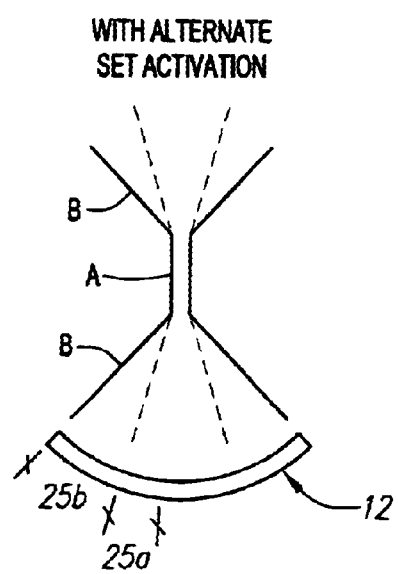
Figure 3E:
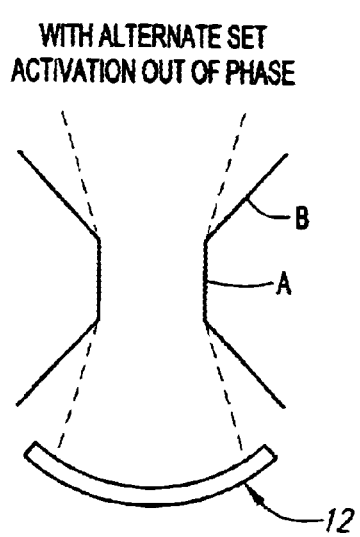

The funnel shapes shown are intended to schematically indicate funnel zones "B" (where the tissue may experience some heating but not necrosis), and the focal zones "A" (corresponding to the desired necrosed region), and may not reflect the actual funnel shapes created by the transducer array. FIGS. 3A and 3B show the funnel shapes created by the array with the entire array activated simultaneously and with apodization, respectively, while FIG. 3C shows the funnel shapes if the array were divided into sectors and driven at mode n. FIGS. 3D and 3E show the shapes of a concentric ring array operated in accordance with the present invention, in mode 0 and mode n, respectively. As may be seen, the focal zones A of FIGS. 3D and 3E are substantially longer than the corresponding focal zones A of FIGS. 3A and 3C, while the width of the funnel zones B that[]are heated, but not necrosed, have similarly wide distributions. While the apodized array of FIG. 3B may have a relatively longer focal zone A, the funnel zones B created are substantially narrower than the funnel zones B shown in FIG. 3D, increasing the risk of undesired heating on either side of the focal zone as compared to a system in accordance with the present invention.

It is well known that the length L of the focal zone of a transducer (i.e., the length of the region A extending between regions B shown in each of FIGS. 3A–3E) is proportional to the wavelength λ of the ultrasonic energy transmitted by the transducer elements and the square of the f-number. This length is defined by:

$$L = k * \lambda * f_n^2,$$

where "k" is a constant, and "$f_n$" is the f-number of the transducer. The constant "k" is fixed based upon the physical configuration of the transducer array, about 6.5 for the exemplary concentric ring transducer arrays described above. Thus, with a fixed wavelength of ultrasonic energy being used, the only parameter that may be varied to change the length "L" is the f-number.

Where only some of the transducer elements, e.g., a plurality of "m" transducer elements, are simultaneously activated, the f-number "$f_m$" is effectively increased, thereby substantially increasing the length L of the focal zone. For example, an increase in f-number of as little as ten percent may increase the length of the focal zone by over twenty percent, simply by deactivating ten percent (in terms of surface area) of the transducer elements on the transducer. By activating only half of the transducer at a time, for example, by dividing a concentric ring array into inner and outer sets as described above, the length of the focal zone may be increased by a factor of four without having to increase the overall energy output of the transducer.

Figure 4:
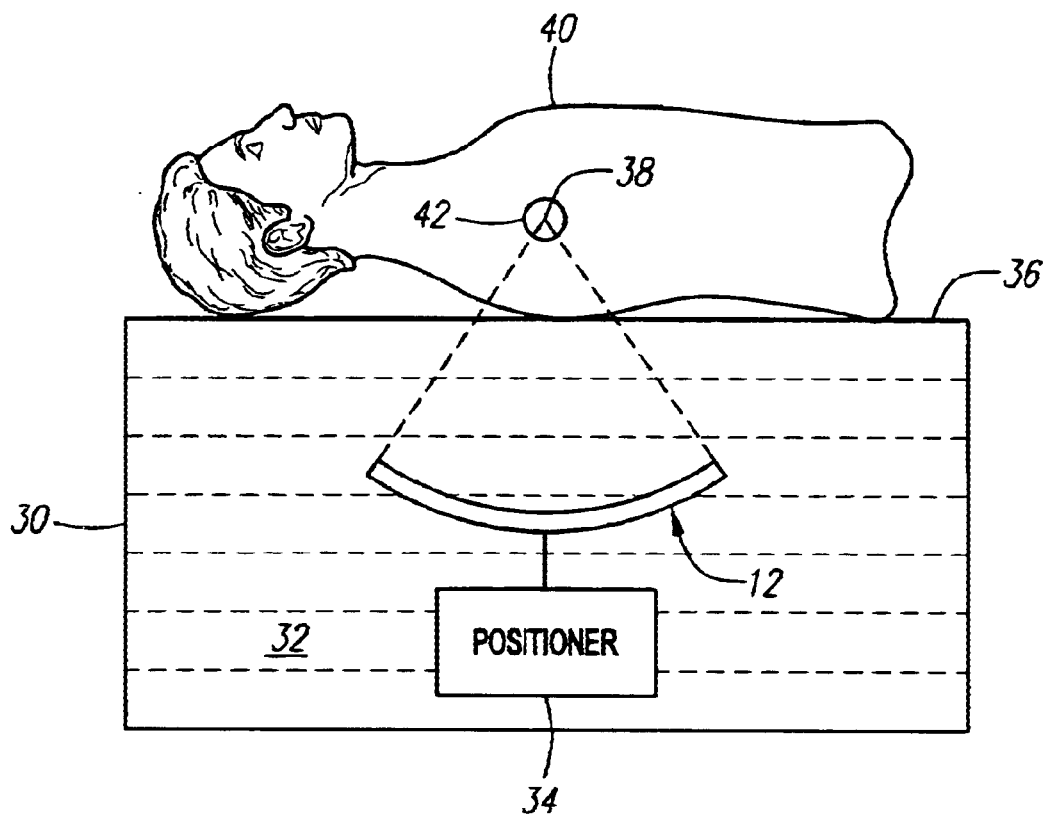
FIG. 4 is a schematic side view of a patient on a water-filled table having an ultrasound transducer array therein.

The use of a system 10 in accordance with the present invention for treating a patient, such as for ablating a benign or cancerous tumor, is shown in FIG. 4. A transducer 12 (such as any of the arrays described above) may be mounted within a fluid-filled casing, such as table 30. The table 30 includes a chamber 32 filled with degassed water or similar acoustically transmitting fluid. The transducer 12 is preferably connected to a positioning system 34 that moves the transducer 12 within the chamber 32, and consequently mechanically adjusts the focal zone 36 of the transducer 12. For example, the positioning system 34 may be configured to move the transducer 12 within the chamber 32 in any one of three orthogonal directions, e.g., horizontally forward and backward, horizontally side-to-side, and vertically. U.S. Pat. Nos. 5,247,935 issued to Cline et al. and U.S. Pat. No. 5,275,165 issued to Ettinger et al., the disclosures of which are expressly incorporated herein by reference, describe exemplary positioning systems that may be used. Alternatively, the positioning system 34 may simply pivot the transducer 12 about a fixed point within the chamber 45, i.e., to change the angle of the transducer 12 and consequently the focal zone 36 with respect to a horizontal plane (not shown). In this alternative, the focal distance of the focal zone may be controlled electronically by changing the phase and/or amplitude of the drive signals 15 provided to the transducer 12, as described above. In further alternatives, the positioning system 34 may move the transducer 12 in a horizontal plane perpendicular to the line of propagation (not shown), with the focal distance controlled electronically, or other combinations of mechanical and electronic positioning may be used, as will be appreciated by those skilled in the art.

The top of the table 30 includes a flexible membrane 38 that is substantially transparent to ultrasound, such as a mylar, polyvinyl chloride (PVC), or other plastic sheet. In addition, a fluid-filled bag (not shown) is generally provided along the top of the table that may conform easily to the contours of a patient placed on the table. In a further alternative, the transducer 10 may be mounted in a fluid-filled bag mounted on a movable arm (not shown) that may be placed in contact with a patient, such as that disclosed in U.S. Pat. No. 5,526,814, the disclosure of which is expressly incorporated herein by reference.

In addition, the system 10 may include an imaging device (not shown) for monitoring the use of the system during treatment of a patient. For example, the system 10 may be placed within a magnetic resonance imaging. (MRI) device, such as that disclosed in U.S. Pat. Nos. 5,247,935, 5,291, 890, 5,368,031, 5,368,032, 5,443,068 issued to Cline et al., and U.S. Pat. Nos. 5,307,812, 5,323,779, 5,327,884 issued to Hardy et al., the disclosures of which are expressly incorporated herein by reference.

Returning to FIG. 4, during use, a patient 40 may be disposed on the table 30 with water, ultrasonic conducting gel, and the like applied between the patient 30 and the bag or membrane 38, thereby acoustically coupling the patient 30 to the transducer 12. The transducer 12 may be focused towards a target tissue region within a tissue structure 42, which may, for example, be a cancerous or benign tumor. The transducer 12 may be activated by alternatively supplying sets of drive signals 15 to the respective sets 25 of transducer elements 22 while focusing the generated ultrasonic energy at the target tissue region 42. The transducer 12 may be activated for sufficient time to substantially necrose the target tissue region 42, e.g., for about 10 seconds or more.

The transducer 12 may be deactivated, for example, for sufficient time to allow heat absorbed by the patient's tissue to dissipate, e.g., for about 60 seconds or more. The transducer 12 may then be focused on another target tissue region (not shown), for example, adjacent to the target tissue region 42, and the process repeated until the entire target tissue structure is ablated.

In an alternative embodiment, a shutter device (not shown) may be disposed between the transducer 12 and the patient 40, for example, mounted above the transducer 12 within the table 30. The shutter device may include a plurality of mechanical shutters that may be controlled by the controller (not shown in FIG. 4) to selectively open and close. Each of the shutters may correspond to one or more individual transducer elements on the transducer 12,such that when the respective shutter is open, the ultrasonic energy produced by the respective transducer element(s) passes freely therethrough to the patient. When the respective shutter is closed, the ultrasonic energy produced by the respective transducer element(s) is blocked or deflected away, and does not reach the patient.

Preferably, the shutter device has an arrangement of shutters that has a different configuration than the transducer elements of the transducer array. Each shutter may overlie a plurality of transducer elements or only a portion of an individual transducer element. For example, the shutter device may include shutters that each obstruct alternating halves of each transducer element. The shutters may then be controlled to alternately cover each half of the respective transducer element, thereby doubling the f-number and the length of the focal zone. Thus, a shutter device may be overlaid over a transducer array to effectively increase the number of transducer elements with a given transducer configuration. Alternatively, a lens device may be provided instead of a shutter device, such as the acoustic lens disclosed in application Ser. No. 09/557,185, which was filed on the same date and assigned to the same assignee as the present application, the disclosure of which is expressly incorporated herein by reference. Thus, a mechanical device may also be used to alternately activate sets of transducer elements, rather than having the controller control the activation electronically.

In a further alternative, a single element transducer (not shown) may be provided and a shutter device (also not shown) may be used to mechanically expose the patient to less than all of the surface area of the transducer at any given moment during a sonication, thereby effectively increasing the f-number of the transducer during a sonication. For example, the shutter device may simply be a disk, having a diameter similar to the cross-section of the transducer, with one or more openings, e.g., pie-shaped openings, provided through the disk (not shown). The disk may be rotatably disposed above the transducer such that, as it rotates, only the surface area of the transducer aligned with the openings are exposed to the patient. The size of the opening may be fixed, or alternatively, the size of the opening may be variable, such that the exposed surface area "a" may be varied during the course of a sonication.

Because only a portion of the surface area of the transducer is exposed at any one time during a sonication, the f-number is effectively increased, and consequently, the length of the focal zone is substantially increased. For example, if an opening (or openings) is provided that has a cross-sectional area "a" that is equal to one quarter the surface area "A" of the transducer, the effective f-number of the transducer may be doubled, and the length of the focal zone may be quadrupled.

In a further alternative, a shutter device or lens having a plurality of shutters may be used in conjunction with a single element transducer (not shown). One or more of the shutters may be selectively opened to expose the patient to alternative surface areas "a" of the transducer. The alternative surface areas "a" may be substantially similar to one another (for example, by providing similar size shutters and opening them one at a time), or the size and shape of the surface areas "a" may be varied during the course of the sonication (for example, by opening multiple shutters or providing different size shutters in the shutter device).

By properly controlling the shutter device, ultrasonic energy may be directed from alternative surface areas "a" of the transducer during a sonication towards the target tissue region via different paths. Thus, because the ultrasonic energy travels through different paths towards the focal zone, undesired heating, particularly in the near field, may be distributed through different tissue regions, thereby minimizing discomfort to the patient and/or damage of tissue outside the focal zone.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

What is claimed is:

1. A system for performing a therapeutic procedure in a target tissue region of a patient using focused ultrasound, comprising:

a transducer array comprising a plurality of "n" transducer elements;

drive circuitry coupled to the transducer elements, the drive circuitry configured for providing sets of respective drive signals to each of the transducer elements; and a controller coupled to the drive circuitry, the controller configured for alternatively focusing ultrasonic energy from a plurality of sets of the transducer elements at a target tissue region within a patient being treated during a single sonication, each set of transducer elements including a plurality of "m" transducer elements, with "m" being less than "n,"

wherein the controller is further configured for dividing the transducer array into "p" sets of transducer elements during the single sonication, "p" being greater than one, each of the "p" sets of transducer elements including "n/p" transducer elements.

2. The system of claim 1 wherein the transducer elements comprise a plurality of concentric rings, and wherein the sets of transducer elements comprise first and second sets of the concentric rings.

3. The system of claim 2, wherein each of the concentric rings is divided circumferentially into a plurality of curved elements.

4. The system of claim 3, wherein the controller is further configured for controlling at least one of delay and amplitude of respective drive signals provided to the curved elements to provide a predetermined size and shape of a focal zone created by the transducer elements.

5. The system of claim 1, wherein the controller is further configured for controlling at least one of delay and amplitude of the respective drive signals to focus the transducer elements in each of the plurality of sets substantially at a desired focal zone.

6. A system for performing a therapeutic procedure in a target tissue region of a patient using focused ultrasound, comprising:

a transducer array comprising a plurality of "n" transducer elements;

drive circuitry coupled to the transducer elements, the drive circuitry configured for providing sets of respective drive signals to each of the transducer elements; and a controller coupled to the drive circuitry, the controller configured for alternatively focusing ultrasonic energy from a plurality of sets of the transducer elements at a target tissue region within a patient being treated during a single sonication, each set of transducer elements including a plurality of "m" transducer elements, with "m" being less than "n,"

wherein the controller is further configured for dividing the transducer array into "p" sets of transducer elements during the single sonication, "p" being greater than one, each set of transducer elements having an overall surface area "a," where "a" equals "A/p," A being an aperture area of the entire transducer array, such that an f-number of each set is substantially greater than an f-number of the entire transducer array the f-number being a ratio of a radius of curvature of the transducer array to a cross-sectional dimension of the transducer array.

7. A method for performing a therapeutic procedure in a target tissue region of a patient using focused ultrasound, the method comprising:

providing a transducer array comprising a plurality of sets of transducer elements, the plurality of gets including all of the transducer elements of the transducer array; and alternatively driving each of the sets of transducer elements with a set of respective drive signals for a predetermined duration during a single sonication, while substantially continuously focusing ultrasonic energy produced by the transducer elements of each set at a desired focal zone, wherein the predetermined duration for which each set of transducer elements is alternatively driven is not more than about one second.

8. The method of claim 7, wherein the sonication has a duration of at least about five seconds.

9. The method of claim 7, wherein the step of alternatively driving each of the sets of transducer elements comprises alternatively coupling each of the sets of transducer elements to drive circuitry that provides the respective drive signals.

10. The method of claim 7, wherein each of the sets of transducer elements has an overall surface area that is substantially the same as one another such that the ultrasonic energy produced by each set is substantially the same as one another.

11. The method of claims 7, wherein the transducer array includes a plurality of "n"transducer elements, and wherein the method further comprises selecting a plurality of "m"transducer elements to include in each of the sets before each of the sets is alternatively driven, "m"being less than "n."

12. The method of claim 7, further comprising randomly assigning a plurality of the transducer elements to each of the sets of transducer elements before each of the sets are alternatively driven.

13. A system for performing a therapeutic procedure in a target tissue region of a patient using focused ultrasound, comprising:

a transducer having a surface area "A" and an f-number, the transducer being configured for emitting ultrasonic energy towards a focal zone, the f-number being a ratio of a radius of curvature of the transducer to a cross-sectional dimension of the transducer;

drive circuitry coupled to the transducer, the drive circuitry configured for providing drive signals to the transducer to cause the transducer to emit ultrasonic energy; and a shutter device disposed between the transducer and the focal zone, the shutter device being configured for exposing the focal zone to alternative surface areas "a" of the transducer, "a" being less than "A."

14. The system of claim 13, wherein the transducer comprises a plurality of "n" transducer elements.

15. The system of claim 14, further comprising a controller coupled to the drive circuitry, the controller configured for controlling the drive circuitry to alternatively provide sets of transducer elements with respective drive signals, each set of transducer elements including a plurality of "m" transducer elements, with "m" being less than "n."

16. The system of claim 13, wherein the shutter device comprises a plurality of shutters.

17. The system of claim 16, further comprising a controller for selectively opening one or more of the plurality of shutters to expose the focal zone to alternative surface areas "a" of the transducer.

18. The system of claim 13, wherein the shutter device comprises an opening therethrough having a cross-sectional area "a", and wherein the shutter device is movable to expose the focal zone to alternative surface areas of the transducer through the opening.

19. A method for performing a therapeutic procedure in a target tissue region of a patient using focused ultrasound, the method comprising:

providing a transducer configured for emitting ultrasonic energy having a surface area "A;"

driving the transducer with drive signals for a predetermined duration during a single sonication, while substantially focusing ultrasonic energy produced by the transducer at the target tissue region; and alternatively directing ultrasonic energy from a plurality of surface areas "a" of the transducer, "a" being less than "A," during the single sonication while substantially focusing the ultrasonic energy at the target tissue region.

20. The method of claim 19, wherein the transducer comprises a plurality of "n" transducer elements, and wherein the step of directing ultrasonic energy comprises alternatively driving a plurality of "m" transducer elements with the drive signals, wherein "m" is less than "n".

21. The method of claim 19, wherein the surface area "a" is periodically changed during the sonication.

22. A method for performing a therapeutic procedure in a target tissue region of a patient using focused ultrasound, the method comprising:

providing a transducer configured for emitting ultrasonic energy having a surface area "A;"

driving the transducer with drive signals for a predetermined duration during a sonication, while substantially focusing ultrasonic energy produced by the transducer at the target tissue region; and alternatively directing ultrasonic energy from surface areas "a" of the transducer, "a" being less than "A," during the sonication towards the target tissue region;

wherein a shutter device is disposed between the transducer and the patient, and wherein the step of alternatively directing ultrasonic energy comprises controlling the shutter device to expose at the patient to surface areas "a" of the transducer through the shutter device.

23. The method of claim 22, wherein the step of controlling the shutter device comprises selectively opening one or more shutters on the shutter device to expose the patient to a surface area "a" of the transducer aligned with the open shutters.

24. The method of claim 22, wherein the shutter device comprises one or more openings therethrough having a total cross-sectional area "a," and wherein the step of controlling the shutter device comprises moving the one or more openings to expose the patient to surface areas "a" aligned with the one or more openings.

* * * * *